(12) United States Patent
Dollat et al.

(10) Patent No.: US 9,238,009 B2
(45) Date of Patent: Jan. 19, 2016

(54) STABLE FAT-SOLUBLE ACTIVE PRINCIPLE PARTICLES

(75) Inventors: Jean-Marie Dollat, Montlucon (FR); Bernard Daffis, Neris les Bains (FR)

(73) Assignee: ADISSEO FRANCE S.A.S., Antony (FR)

( * ) Notice: Subject to any disclaimer, the term of this patent is extended or adjusted under 35 U.S.C. 154(b) by 0 days.

(21) Appl. No.: 13/505,363

(22) PCT Filed: Dec. 9, 2010

(86) PCT No.: PCT/FR2010/052656
§ 371 (c)(1),
(2), (4) Date: Jun. 1, 2012

(87) PCT Pub. No.: WO2011/070300
PCT Pub. Date: Jun. 16, 2011

(65) Prior Publication Data
US 2012/0237604 A1    Sep. 20, 2012

(30) Foreign Application Priority Data

Dec. 9, 2009  (FR) ..................................... 09 58779

(51) Int. Cl.

| | |
|---|---|
| A61K 9/50 | (2006.01) |
| A23K 1/00 | (2006.01) |
| A23K 1/16 | (2006.01) |
| A23K 1/175 | (2006.01) |
| A23K 1/18 | (2006.01) |
| A23L 1/00 | (2006.01) |
| A23L 1/30 | (2006.01) |
| A23L 1/302 | (2006.01) |
| A23L 1/303 | (2006.01) |
| A23L 1/304 | (2006.01) |
| A61L 9/16 | (2006.01) |
| A23P 1/04 | (2006.01) |
| A61K 9/16 | (2006.01) |

(52) U.S. Cl.
CPC ............... *A61K 9/5057* (2013.01); *A23K 1/004* (2013.01); *A23K 1/1603* (2013.01); *A23K 1/1753* (2013.01); *A23K 1/1758* (2013.01); *A23K 1/184* (2013.01); *A23L 1/0029* (2013.01); *A23L 1/0032* (2013.01); *A23L 1/3002* (2013.01); *A23L 1/302* (2013.01); *A23L 1/303* (2013.01); *A23L 1/304* (2013.01); *A23L 1/3008* (2013.01); *A23P 1/045* (2013.01); *A61K 9/1658* (2013.01); *A61K 9/1694* (2013.01); *A61K 9/5089* (2013.01)

(58) Field of Classification Search
CPC .... A23K 1/004; A23K 1/1603; A23L 1/0029; A23L 1/3008; A23L 1/302; A23L 1/303; A23L 1/304; A23P 1/045; A61K 9/1658; A61K 9/1694; A61K 9/5057; A61K 9/5089
See application file for complete search history.

(56) References Cited

U.S. PATENT DOCUMENTS

| | | | | |
|---|---|---|---|---|
| 4,921,705 | A | * | 5/1990 | Arai et al. ...................... 424/450 |
| 5,153,177 | A | * | 10/1992 | Chaundy et al. ............... 514/5.5 |
| 6,328,995 | B1 | * | 12/2001 | Bewert et al. .................. 424/489 |
| 2006/0051479 | A1 | * | 3/2006 | Chiavazza et al. ............. 426/541 |

FOREIGN PATENT DOCUMENTS

| | | |
|---|---|---|
| EP | 0494417 A2 | 7/1992 |
| WO | 2004057980 A1 | 7/2004 |
| WO | WO 2004057980 A1 * | 7/2004 |

OTHER PUBLICATIONS

Serajuddin (Journal of Pharmaceutical Sciences, 2000, vol. 88, pp. 1058-1066).*

* cited by examiner

*Primary Examiner* — Sean Basquill
*Assistant Examiner* — Mark V Stevens
(74) *Attorney, Agent, or Firm* — Porzio, Bromberg & Newman, P.C.

(57) ABSTRACT

A method for preparing fat-soluble active ingredients, including the steps of preparing an oil-in-water emulsion including 8 to 20% of at least one protein, 5 to 15% of at least one sugar, 0.5 to 3% of at least one inorganic salt, 10 to 22% of at least one fat-soluble active ingredient in an oily form and/or dissolved in an edible oil, and qsp % of water, shaping of particles in a substantially spherical shape by the dispersing the oil-in-water emulsion obtained at the end of step a) in a fluid, adding at least one agent for cross-linking of the at least one protein to the dispersion obtained at the end of step b), and the active ingredients are recovered with the substantially spherical shape.

14 Claims, 1 Drawing Sheet

STABLE FAT-SOLUBLE ACTIVE PRINCIPLE PARTICLES

CROSS REFERENCE TO RELATED APPLICATION

This is a National Stage of International Application No. PCT/FR2010/052656, filed 9 Dec. 2010, which claims the benefit of Application No. 0958779, filed in France on 9 Dec. 2009, the disclosures of which Applications are incorporated by reference herein.

The present invention relates to fat-soluble food and/or medicinal active ingredients as particles which not only have good storage stability, but also in a mixture in a pre-mix of additives which contains aggressive agents, most particularly intended for animal nutrition.

The present invention more specifically relates to the preparation of compounds based on vitamins and/or carotenoids and/or derivatives thereof.

Vitamins and carotenoids in the form of particles (or in other words of powders) are very widely used in many technical fields such as the pharmaceutical industry, the agrifood industry, and notably in the field of animal nutrition. As an example, vitamins A and E are currently used for preparing foodstuffs promoting growth of animals. These foodstuffs are however prepared by means of methods applying extreme conditions, such as high temperatures, high humidity, high pressures and high mechanical stresses, which may be damageable to the active ingredients, and in particular to the vitamins present in these foodstuffs.

Moreover, both in pharmacy and in animal nutrition, it is important that said active ingredient should not be degraded as soon as it encounters the first severe, notably acid, conditions, upon entering the digestive system.

This is why, in order to preserve at best these active ingredients sensitive to these aforementioned extreme conditions, it has been known for a long time how to protect them by mixing them with proteins such as gelatin and by causing cross-linking of these proteins around these active ingredients.

But vitamin A in the form of acetate or vitamin E are oily products which only mix with the proteins and their cross-linking agent in the form of an oil-in-water emulsion which is never easy to handle.

In this respect, various methods for cross-linking the proteins in the presence of vitamin A have been described.

Document EP A 0 261 616 describes a method for cross-linking gelatin in the presence of acetaldehyde for protecting vitamin A. More specifically, a mixture is made which comprises a protein, an alcohol miscible with water, acetaldehyde, water and vitamin A in the form of drops with a size of less than 10 μm. This mixture is freeze-dried so as to obtain solid particles with a diameter comprised between 100 and 800 microns.

The thereby obtained solid particles are then subject to acetaldehyde vapors for a period of about 3 hours at a temperature comprised between 60 and 90° C. Nevertheless, this method cannot be carried out continuously, since it requires two steps, each of them requiring a different type of apparatus, i.e. a freeze-drier and a spraying apparatus.

Freeze-drying is a costly step and the productivity of which is extremely limited.

Also, according to the method for preparing spherules of vitamin A described in document EP A 0 285 682, it is known how to prepare an emulsion containing a vitamin, water, gelatin and a sugar which is transformed into droplets by spraying. These droplets are then individually put into contact with a cellulose powder having well defined characteristics until the droplets harden. The thereby hardened droplets are then separated from the cellulose powder by sifting, the sieve having to retain the hardened droplets and let through the powder; which requires a strict selection of the grain size of the cellulose powder and especially of its nature so that it does not agglomerate during the application of the method. The recovered droplets are then dried, and then subject to a heating operation in order to ensure cross-linking of the gelatin by reaction of the amine groups of the gelatin with the reducing functions of the sugar. This method is particularly difficult to apply because of the strict selection of the materials used and of closer monitoring of the application conditions.

From the methods described above, it emerges that the cross-linking of the protein requires heating to quite high temperatures and furthermore for a relatively long period, which is hardly compatible with the stability of vitamins under these conditions.

Document EP A 1 088 486 attempts to find a remedy to these drawbacks by proposing a method for preparing stable dry powders containing fat-soluble vitamins and/or carotenoids applying a cross-linking step under less drastic conditions, i.e. during a short reaction time, preferentially less than half an hour. Indeed, this preparation method comprises the following steps:

a step for making an aqueous dispersion comprising a protein, a sugar, an alkaline metal phosphate salt and a vitamin (or carotenoid), followed by a step for transforming this dispersion into a dry powder, notably by drying, and then a cross-linking step consisting in a heat treatment of the protein at a temperature comprised between 55° C. and 180° C., but preferentially between 85° C. and 125° C., for a duration comprised between 5 minutes and 3 hours, preferably between 6 and 25 minutes.

The fact remains that the sensitive active ingredients, such as vitamins, may also be subject to damages during their mixing with aggressive agents such as metal salts (for example sulfates, iodates, carbonates) or further oxides during the preparation of the pre-mix, consequently said to be <<aggressive>>, and which are intended for animal nutrition. Thus it is also indispensable to protect these sensitive active ingredients against damages caused by sulfates such as cobalt, copper, iron sulfates, carbonates such as iron carbonates, iodates such as calcium iodates or further against certain oxides such as green manganese oxide or zinc oxides or further compounds based on selenium. Indeed, these aggressive agents may react according to oxidation-reduction reactions with the active ingredients such as vitamins and therefore degrade them.

The present invention proposes to find a remedy to these difficulties in the preparation of fat-soluble active ingredients, and in particular of vitamins, which have been detailed in the state of the art above. Indeed, the present invention proposes a novel method for preparing fat-soluble active ingredients which, in addition to their excellent stability properties under extreme conditions during industrial processes and during their storage, have good stability when they are mixed in so-called <<aggressive>> pre-mixes. Further, unlike some of the aforementioned preparation methods, like the one described in document EP A 1 088 486, the preparation method according to the present invention has the advantage of not including any heat treatment step for achieving the step for cross-linking the protein applied during this method. Indeed, cross-linking may be carried out under so-called <<mild>> conditions, i.e. at not very high temperatures, of the order of 60° C.

Further, the thereby obtained active ingredients according to the invention exhibit excellent insolubility properties in hot water above 60° C. Now, as this is known to one skilled in the art, this insolubility property in hot water is significant in that the thereby obtained formulations will be quite stable in the methods for preparing foodstuffs with presses for granulation at temperatures of 80 to 90° C. in a humid medium. On the other hand, this particularity is put to good use in order to use these formulations in foodstuffs for ruminants. Indeed, upon staying several hours in the rumen at 40° C., the active ingredient remains insoluble and will be released in the intestinal portion.

The method for preparing fat-soluble, in particular pharmaceutical and/or food, active ingredients, as particles, comprises the following steps:
  a) an oil-in-water emulsion is prepared comprising in weight percentages based on the total weight of said emulsion:
    8 to 20% of at least one protein, preferentially 10 to 15%,
    5 to 15% of at least one sugar, preferentially 8 to 12%,
    0.5 to 3% of at least one inorganic salt preferentially 2 to 3%,
    10 to 22% of at least one fat-soluble active ingredient in oily form and/or dissolved in an edible oil, preferentially 15 to 20%,
    qsp % of water.
  b) it is proceeded with the shaping of particles in the substantially spherical form by dispersing the oil-in-water emulsion obtained at the end of step a) in a fluid,
  c) at least one agent for cross-linking the protein is added to the dispersion obtained at the end of step b),
  d) the active ingredients are recovered in the form of substantially spherical particles.

The protein may be selected from vegetable or animal proteins. For example, gelatin may be used, in particular pork skin or bone gelatin, as well as bovine gelatin, fish gelatin. The gelatins of type A or B are quite suitable and preferably with a bloom value comprised between 50 and 300. The protein may also be selected from casein or caseinate, or else these may be soya bean or maize proteins.

The sugar may be selected from polyols, monosaccharides, disaccharides, glucose and fructose syrups and maltodextrins. In particular, glycerols, sorbitols, maltitols and xylitol, fructose, glucose, lactose, maltose, xylose, sucrose, arabinose, ribose and saccharose are preferred. Even more preferentially fructose, glucose, glucose syrups and further saccharose are used, taken alone or as mixtures.

The inorganic salt is preferably an alkaline metal phosphate, which may be selected from sodium, potassium, lithium salts of mono-, di-, and tri-phosphoric acid or polyphosphoric acid.

Advantageously, are used:
  sodium phosphate ($Na_3PO_4$), sodium hydrogenphosphate ($Na_2HPO_4$), sodium dihydrogen phosphate ($NaH_2PO_4$), sodium dihydrogen diphosphate, sodium triphosphate, sodium trimetaphosphate ($Na_3P_3O_9$),
    potassium phosphate ($K_3PO_4$), potassium hydrogen phosphate ($K_2HPO_4$), potassium dihydrogen phosphate ($KH_2PO_4$), potassium dihydrogen diphosphate, potassium triphosphate, potassium trimetaphosphate ($K_3P_3O_9$).

Sodium dihydrogen phosphate ($NaH_2PO_4$) is most preferred.

Within the scope of the method according to the invention, use may be made of any active ingredient which may be dissolved or dispersed in an edible oil. By edible oil, is meant both vegetable or animal edible oils. Groundnut, sunflower, rapeseed, maize, soyabean, palm oil or their methyl ester derivatives or cod liver oil are particularly preferred.

The fat-soluble active ingredients may notably be selected from:
  vitamins such as vitamin A, E, D and notably vitamin D3, K and notably vitamin K3, as well as
  derivatives of these vitamins such as their esters and notably esters of vitamins A such as vitamin A acetate, vitamin A propionate or vitamin A palmitate, or further esters of vitamins E such as tocopheryl acetate,
  carotenoids such as beta-carotene, lycopene, bixin, zeaxanthin, citranaxanthin, asthaxanthin, canthaxanthin, lutein, capsanthin, cryptoxanthin, beta-apo-8'-carotenoic acid and its esters, beta-apo-8'-carotenal, beta-apo-12'-carotenal,
    polyunsaturated fatty acids such as omega 3 and omega 6 fatty acids.

Advantageously, vitamins put into solution in an edible oil or else provitamins are used. The vitamins may be pure vitamins of natural or synthetic origin. Vitamins in an oily form, in particular vitamin E and vitamin A are most preferred.

Among the carotenoids, beta-carotene, lycopene, lutein, zeaxanthin, canthaxanthin and asthaxanthin are preferred.

When the fat-soluble active ingredients are sensitive to oxidation, which is often the case in the technical field of animal nutrition, it is particularly advantageous to add at least one antioxidant in the oil-in-water emulsion of step a). The antioxidant agent may be selected from tertiobutyl 3-hydroxyl-4-anisole (BHA), ditertiobutyl-5-hydroxy-4-toluene (BHT), ethoxy-6-dihydroxy-1,2-trimethyl-2,2,4-quinoline (ethoxyquin), tertiobutyl-2-dihydroxy-1,4-benzene or further tocopherol, citric acid or phytic acid and their alkaline metal salts, or further ethylene-diamine-tetra-acetic acid (EDTA).

Further, the oil-in-water emulsion of step a) of the method according to the invention may comprise humidifying agents such as polyethylene glycols, sorbitol or glycerol or an emulsifier such as lecithin.

Also, thickeners such as gum arabic, guar gum, alginates or certain modified starches may be added into the oil-in-water emulsion of step a) in order to adjust the viscosity of the latter.

The preparation of the oil-in-water emulsion of step a) of the method according to the invention may be accomplished in the following way:
  i. In a first mixer, the protein(s) is(are) dissolved in hot water at a temperature comprised between 45° C. and 70° C., preferably between 45° C. and 55° C., more preferentially 50° C., and this with stirring, for example at a speed of 2 to 3 m/s and for at least 20 minutes.
  ii. In this first mixer, the sugar(s), the inorganic salt(s) and the fat-soluble active ingredient(s) are added in an oily form, and optionally antioxidants, as well as at least one of the constituents detailed above as selected from humidifying agents, emulsifiers, thickeners. The temperature is always maintained at a temperature comprised between 45° C. and 70° C., preferably between 45° C. and 55° C., more preferentially 50° C. The mixture is maintained with stirring upon adding the different constituents, for example at a speed from 2 to 3 m/s. In order that the mixture be quite homogeneous, stirring is maintained for at least ten minutes.

Another alternative to the preparation of the oil-in-water emulsion may consist of dissolving in a first mixer, the sugar(s) in hot water at a temperature comprised between 45° C. and 70° C., preferably between 45° C. and 55° C., more preferentially 50° C., and then adding the protein(s) thereto, and this with stirring and so as to obtain a homogeneous mixture. Next, the other constituents which are the inorganic salt(s), the active ingredient(s), and the optional constituents are successively added to the mixture in the first mixer.

Further, quite advantageously, before step a), before adding the active ingredients in the first mixture, the active ingredients in a second mixer are dissolved in an edible oil such as groundnut, sunflower, rapeseed, maize, soya bean, palm or further cod liver oil. And this mixture obtained in this second mixer is then added into the first mixer.

This pre-mix in an edible oil contributes to improvement of the stability of the active ingredients during the application of the steps of the method according to the invention, and then during storage of the product obtained at the end of said method. Indeed, the edible oil initially appears in liquid form. It will be brought to solidification during the method according to the invention and will be found as a solid at the end of said method, and this while coating said active ingredients; which will have the advantage of protecting them during storage.

The step b) of the method according to the invention is a step determining the shape of the particles of active ingredients which will be obtained at the end of said method. A quite advantageous particulate shape corresponds to a shape as spherical as possible and with an adequate size, i.e. which may be comprised between 50 and 630 μm. The selection of the size of the particles may notably depend on the contemplated field of application not on the active ingredients.

Thus, step b) of the method according to the invention is carried out adequately depending on the desired particle size of the product obtained at the end of the method.

The oil-in-water emulsion obtained at the end of step a) may be dispersed during step b) of the method according to the invention into air by atomization, for example within an atomization tower via nozzles or turbines. Advantageously, the air inlet temperature is about 150° C. and the emulsion is atomized at a temperature of the order of 60° C.

In a very advantageous embodiment of the invention, the oil-in-water emulsion obtained at the end of step a) is dispersed during step b) of the method according to the invention, in an edible oil so as to obtain a <<double emulsion>>, i.e. an emulsion (oil-in-water) in oil. This may be an oil selected from groundnut, sunflower, rapeseed, maize, soya bean, palm oil, from their methyl ester derivatives or further from cod liver oil.

In step c) of the method according to the invention, the agent for cross-linking the protein may be selected from acetaldehyde, glutaraldehyde, glyoxal. Glutaraldehyde is preferably used. Further, the cross-linking agent may be used in the pure condition or preferably in an aqueous solution according to a concentration comprised between 5 and 25%. The cross-linking agent reacts with the amine groups of the protein by forming imine bonds. For example, the glutaraldehyde reacts with the amine groups of gelatin by forming imine bonds. Thus, the glutaraldehyde is transformed by being inserted into the gelatin lattice.

If the oil-in-water emulsion was atomized in step b) of the method according to the invention, the addition of at least one cross-linking agent of step c) may be carried out in a fluidized bed with a temperature comprised between 55° C. and 65° C., preferably 60° C.

If the oil-in-water emulsion obtained at the end of step a) was dispersed during step b) of the method according to the invention, in an edible oil so as to obtain a double emulsion, then step c) of the method according to the invention may consist of lowering the temperature of the mixture (or in other words, of the double emulsion) obtained at the end of step b) to a cooling temperature which is less than the phase transition temperature of the protein, so as to solidify the droplets of active ingredients in the edible oil and therefore obtain a dispersion of granules of humid active ingredient (i.e. they comprise between 40 and 60% of water) in the edible oil to which the agent for cross-linking the protein is added at this cooling temperature.

For example, when the protein used in step a) is gelatin, the temperature is lowered to a temperature comprised between 12° C. and 18° C.

If step b) of the method according to the invention consisted in atomization, the major portion of the water of the emulsion has evaporated during step b), this is why step d) of the method according to the invention may consist in drying on a fluidized bed at a temperature comprised between 55° C. and 65° C., preferably at 60° C. in order to complete evaporation of the water, and this in order to recover a powder of active ingredients.

If step b) of the method according to the invention consisted in the preparation of a double emulsion, then the step d) for recovering the active ingredients might consist in the following successive steps:
   the granules of active ingredients thereby obtained at the end of step c) are drained,
   optionally, said granules of active ingredients are absorbed on an anti-agglomerating agent such as silica, magnesium stearate or starch, maltodextrin or corn starch,
   said granules of active ingredients are dried in a fluidized bed at a temperature comprised between 55° C. and 65° C., preferably at 60° C., and this so as to recover particles of active ingredients.

Silica is preferentially used as an anti-agglomerating agent.

Advantageously, the size of the recovered particles at the end of step d) is comprised between 50 and 630 μm.

The thereby obtained particles of the active ingredients at the end of the preparation method according to the invention have a water content comprised between 1 and 5% by weight.

The obtained particles of active ingredients according to the method in accordance with the invention have insolubility in hot water at 60° C.

It should be noted that the whole of the steps of the method for preparing particles of active ingredients according to the invention may be carried out according to a continuous method, for example by means of reactors in cascade, the filling of which is accomplished by overflow of the upstream reactor towards the downstream reactor or by a batch method. It is quite obvious that a continuous method has notable economical advantages.

The invention also relates to fat-soluble particles of in particular pharmaceutical and/or edible, active ingredients, which may be obtained by the method according to the present invention.

Another object of the invention is a pre-mix, in particular an aggressive pre-mix, which comprises particles of fat-soluble active ingredients according to the present invention.

The aggressive pre-mix may comprise in addition to the vitamins, constituents as selected from copper sulfate, calcium carbonate, cobalt sulfate, iron sulfate, iron carbonate, calcium iodate, green manganese oxide, zinc oxide, derivatives of selenium.

The invention also relates to foodstuffs or fodders which contain fat-soluble active ingredient particles according to the invention.

The invention also relates to a food composition comprising particles of fat-soluble active ingredients which may be obtained by the preparation method according to the present invention. These may be food supplements, which for example comprise vitamins, and which are intended to complete the daily intakes required for the body to operate properly.

EXPERIMENTAL PART

Figure 1:
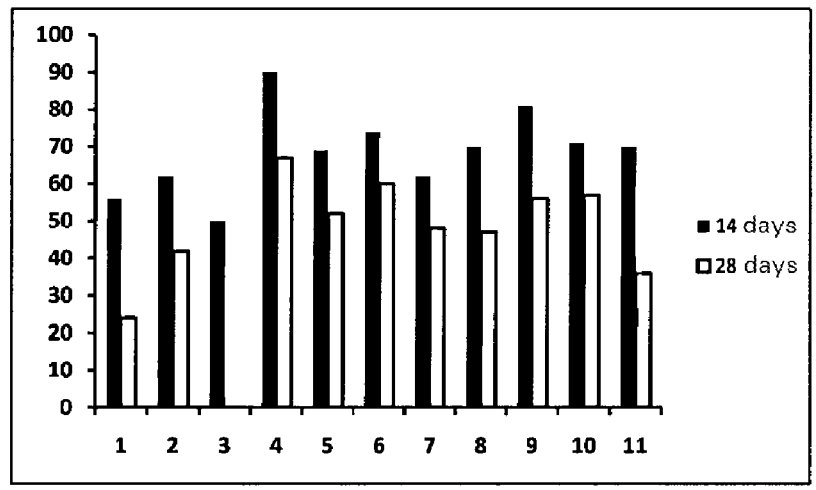
FIG. 1 represents a histogram expressing the recovery rate of vitamin A acetate respectively at 14 and 28 days of the test nos. 1 to 11.

Evaluation of the Stability of Particles Prepared According to the Method in Accordance with the Invention in a Pre-Mix, a So-Called <<Aggressive Pre-Mix>>:

Within the scope of this experimental part, the <<tested>> active ingredient was:
vitamin A acetate (part 1), and then
vitamin A propionate (part II), i.e. compounds sensitive to the industrial process conditions described above, as well as mixed in an aggressive pre-mix.

It should be noted that in the mixtures described below, vitamins are part of the constituents of the compositions. Indeed, it is not necessary to prepare in accordance with the method according to the invention, all the vitamins entering the composition of a pre-mix, in particular those which are not too sensitive to extreme conditions, and this in order to limit the production costs of the pre-mix.

I. Tested Active Ingredient: Vitamin A Acetate:

A—Preparation of the Vitamin A Acetate Active Ingredient

For all the tests 1 to 11, in a mixer, gelatin was dissolved in water at 50° C. with stirring at a speed of 2 to 3 m/s, and this for about 20 minutes.

A sugar, vitamin A acetate, di-tertiobutyl-5-hydroxy-4-toluene (BHT) were then added into this first mixer, still with stirring at 2 to 3 m/s.

$NaH_2PO_4$ was further added only for the tests nos. 4 to 11.

The temperature of the mixer was still maintained at 50° C., and this until a homogeneous mixture is obtained.

In this thereby obtained homogeneous mixture, water represented by weight about 50% of said mixture.

The emulsion obtained in tests 1 to 11 was then dispersed in rapeseed oil methyl ester.

Next, for the tests 1 to 10, the temperature of the mixer was lowered to a temperature comprised between 12° C. and 18° C., and glutaraldehyde was added as an agent for cross-linking the protein. Humid granules of vitamin A acetate were thus obtained. These humid granules were then drained and absorbed on silica, and then dried in a fluidized bed at a temperature of 60° C. Ten powders of vitamin A acetate from tests 1 to 10 were then recovered (or in other words, particles of vitamin A acetate from tests 1 to 10).

As regards test no. 11, after the emulsion obtained from the mixture of the constituents of this test was dispersed in rapeseed oil methyl ester, these humid granules were drained and absorbed on silica, and then dried in a fluidized bed at a temperature of 60° C. Next, thermal cross-linking was carried out at 100° C. A powder of vitamin A acetate of this test no. 11 was thereby obtained.

In Table 1 below, the amount and the nature of the different constituents which make up the powders of test numbers 1 to 11 consist, obtained as described above, are recapitulated. The percentages are expressed by weight based on the total composition.

It should be noted that a subtotal is expressed corresponding to the sum of the percentages of:
active ingredient,
antioxidant,
protein,
sugar,
optionally inorganic salt.

The other constituents of these test powders 1 to 11 are the silica used during absorption, the residual water after drying, the oil used, i.e. rapeseed oil methyl ester, for making the double emulsion. The percentages expressed by weight of these three last constituents are of the order of 2, 3 and 2%, respectively, according to the different tests. This is why mention is made in Table 1 of <<qsp % [silica+water+rapeseed oil methyl ester]>>.

Further, as explained above with regard to the agent for cross-linking the protein, the glutaraldehyde reacts with the amine groups of gelatin by forming imine bonds. The glutaraldehyde is therefore transformed, and this is why this constituent is not found in Table 1, which recapitulates the final composition of the particles obtained at the end of the preparation method.

Tests 1 to 3 are comparative tests. Indeed, as described above, no $NaH_2PO_4$ was added in these tests 1 to 3.

Tests 4 to 10 were conducted according to the present invention.

Moreover, unlike the tests 1 to 10, the antioxidant used for test no. 11 was ethoxyquin.

Test no. 11 is also a comparative test relative to the present invention, given that for this test, thermal cross-linking of the protein was applied, unlike tests 1 to 10 in which it was proceeded with chemical cross-linking of the protein (i.e. by adding glutaraldehyde).

TABLE 1

| | | percentages or the different constituents according to the test | | | | | | | | | | |
|---|---|---|---|---|---|---|---|---|---|---|---|---|
| | | Test No. % Constituents | | | | | | | | | | |
| | | N° 1 | No. 2 | No. 3 | No. 4 | No. 5 | No. 6 | No. 7 | No. 8 | No. 9 | No. 10 | No. 11 |
| Active ingredient | Vitamin A acetate | 38.5 | 39.0 | 37.7 | 38.3 | 38.3 | 36.5 | 38.3 | 39.2 | 38.3 | 37.2 | 37.2 |
| Antioxidant | BHT | 10.0 | 20.5 | 28.3 | 17.8 | 17.8 | 17 | 18.5 | 18.3 | 22.6 | 23.1 | 4 |
| Protein | Gelatin 140 BI | 21.7 | 0 | 0 | 0 | 0 | 0 | 0 | 21.9 | 0 | 23.3 | 35.1 |
| | Gelatin 220 BI | 0 | 0 | 0 | 0 | 18.5 | 17.6 | 18.5 | 0 | 0 | 0 | 0 |
| | Gelatin 300 BI | 0 | 19.5 | 17.9 | 18.5 | 0 | 0 | 0 | 0 | 17.9 | 0 | 0 |
| Sugar | Glucose syrup | 23.5 | 14.7 | 9.9 | 14.0 | 14 | 13.3 | 14 | 9.3 | 10 | 0 | 0 |
| | Meliose | 0 | 0 | 0 | 0 | 0 | 0 | 0 | 0 | 0 | 5 | 8.1 |

TABLE 1-continued percentages or the different constituents according to the test

| | | Test No. % Constituents | | | | | | | | | | |
|---|---|---|---|---|---|---|---|---|---|---|---|---|
| | | N° 1 | No. 2 | No. 3 | No. 4 | No. 5 | No. 6 | No. 7 | No. 8 | No. 9 | No. 10 | No. 11 |
| Inorganic salt | NaH$_2$PO$_4$ | 0 | 0 | 0 | 5.2 | 5.2 | 4.9 | 5.2 | 4.8 | 5 | 5 | 5 |
| Subtotal | | 93.7 | 93.7 | 93.8 | 93.8 | 93.8 | 94.3 | 94.5 | 93.5 | 93.8 | 93.6 | 94.4 |
| Total | | qsp % [silica + water + rapeseed oil methyl ester] | | | | | | | | | | |

All the powders of tests 1 to 11 were then mixed with a so-called <<aggressive>> mixture with 6,000 i.u./g of vitamin A acetate which was prepared as detailed hereafter.

B—Preparation of an Oligopork Pre-Mix:

A so-called <<oligopork>> pre-mix, i.e. intended for porcine nutrition, was prepared by mixing together the following constituents (the indicated percentages represent the weight percentages relatively to the total composition of the oligopork pre-mix):
cobalt sulfate: 0.39%;
copper sulfate: 10%;
iron sulfate: 12.5%;
iron carbonate: 20%;
calcium iodate: 0.15%;
green manganese oxide: 10.7%;
zinc oxide: 24.9%;
a selenium derivative (trade name: SELENIPHOS) 0.60%;
qsp % of calcium carbonate.

C—Preparation of a Complex:

A mixture of active ingredients, designated as <<complex>> hereafter was prepared in the following way (the amounts are expressed in g):
The following constituents were mixed together:
vitamin D3 at 500 i.u/g: 0.400 g
vitamin E at 50%: 3.840 g
vitamin B1: 0.128 g
vitamin B2: 0.384 g
calcium panthothenate: 0.960 g
vitamin K3 at 96%: 0.128 g
vitamin B6: 0.128 g
vitamin B12 at 0.1%: 1.280 g
niacin: 1.920 g
vitamin B9: 0.064 g
calcium carbonate: 3.750 g
middlings: 1.600 g D—Preparation of an Aggressive Pre-Mix at 6,000 i.u./g:

An aggressive pre-mix was prepared by mixing together the following constituents (the amounts are expressed in g):
oligopork pre-mix (as described above): 24.0 g
choline chloride at 50%: 38.4 g
copper sulfate: 22.4 g
calcium carbonate: 59.2 g
omplex (described above): 14.6 g That is to say, a mixture of a total weight of 158.6 g, to which were added 0.95 g of vitamin A acetate powder as prepared above according to tests 1 to 11.

In order to demonstrate the good stability properties of a vitamin A acetate powder, prepared according to the method in accordance with the invention (tests 4 to 10), the recovery rate of this vitamin A acetate was measured after 14 and 28 days, and compared with that measured for a vitamin A acetate powder not prepared according to the invention (tests 1 to 3 and 11).

In order to carry out these measurements of the recovery rate, the powders of the tests 1 to 11 were placed in an enclosure, maintained at a temperature of 30° C. and under a relative humidity of 75%.

The analyses of the vitamin A acetate content were carried out after extraction, and then by assaying with high performance liquid chromatography (HPLC):
isocratic chromatograph equipped with a pump which may deliver 1.2 mL/min,
an injection valve of the RHEODYNE type,
a UV detector,
a column: Lichrocart 125-4, Lichrosorb Si 60 (5 μm),
mobile phase: n-hexane (99.5%)/2-propanol (0.05%).

Thus, the higher the percentage of the recovery rate, the more significant is that the vitamin A acetate was not degraded in the aggressive pre-mix. Table 2 recapitulates the obtained results.

TABLE 2 expressing the recovery rates of vitamin A acetate at 14 and 28 days according to tests 1 to 11.

| | Recovery rate (%) | | | | | | | | | | |
|---|---|---|---|---|---|---|---|---|---|---|---|
| | No. 1 | No. 2 | No. 3 | No. 4 | No. 5 | No. 6 | No. 7 | No. 8 | No. 9 | No. 10 | No. 11 |
| 14 days | 56 | 62 | 50 | 90 | 69 | 74 | 62 | 70 | 81 | 71 | 70 |
| 28 days | 24 | 42 | N.D. | 67 | 52 | 60 | 48 | 47 | 56 | 57 | 36 |

The recovery rate of test No. 3 was not measured at 28 days.

This Table 2 shows the good stability of the obtained vitamin A acetate powders according to the preparation method of the invention relative to the comparative tests 1 to 3 and 11.

At 28 days, the recovery rate of the tests according to the invention is always greater than that of the comparative tests.

FIG. 1 illustrates a histogram expressing the recovery rate of vitamin A acetate at 14 and 28 days respectively of tests nos. 1 to 11 which are indicated in the Table 2 above.

II. Tested Active Ingredients: Vitamin A Propionate:

E—Preparation of the Active Ingredient, Vitamin A Propionate:

The active ingredient, vitamin A propionate, was prepared in the same way as the vitamin A acetate described above. The nature and the amount of the different constituents of the tests nos. 12 to 14 are recapitulated in the Table 3 below and are expressed as percentages by weight relative to the total composition.

TABLE 3

Percentages of the different constituents according to the test.

| Constituent | Test | No. 12 | No. 13 | No. 14 |
|---|---|---|---|---|
| Active ingredient | Vitamin A propionate | 40.2 | 39.9 | 39.9 |
| Antioxidant | BHT | 9.8 | 9.4 | 10.3 |
| Protein | Gelatin 140 Bl | 0 | 0 | 21.5 |
|  | Gelatin 220 Bl | 21.7 | 21.6 | 0 |
|  | Gelatin 300 Bl | 0 | 0 | 0 |
| Sugar | Glucose syrup | 23.6 | 19.1 | 0 |
|  | Meliose | 0 | 0 | 19.1 |
| Inorganic salt | $NaH_2PO_4$ | 0 | 4.9 | 3 |
|  | Subtotal | 94.9 | 94.9 | 93.8 |
|  | Total | | qsp % [silica + eau + rapeseed oil methyl ester] | |

Test no. 12 is a comparative test. Indeed, as described above, no $NaH_2PO_4$ was added in this test.

Tests nos. 13 and 14 were conducted according to the present invention.

The same aggressive pre-mix for vitamin A acetate was prepared. A mixture was therefore obtained, as described above with a weight of 158.6 g to which were added 0.95 g of vitamin A propionate powder as prepared above according to tests 12 to 14.

For tests 12 to 14, the recovery rate of vitamin A propionate was measured according to the same procedure as the one described for tests 1 to 11.

Table 4 below recapitulates the the obtained results as regards the recovery rate of vitamin A propionate.

| Recovery rate (%) | N°12 | N°13 | N°14 |
|---|---|---|---|
| 14 days | 49 | 72 | 74 |
| 28 days | N.D. | 61 | 46 |

Table 4 expressing the recovery rates for vitamin A propionate at 14 and 28 days according to tests 12 to 14.

The recovery rate of test no. 12 was not measured at 28 days.

A better recovery rate for vitamin A propionate at 14 days is noted for the tests according to the invention than for the comparative tests.

Figure 2:
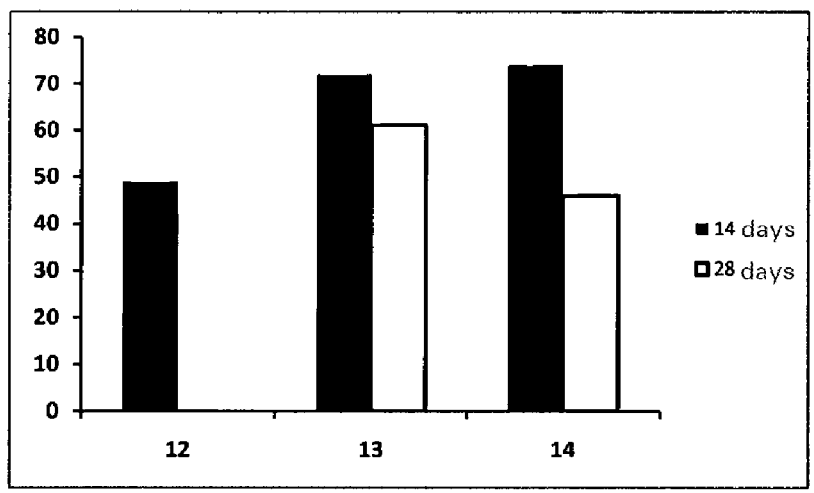
FIG. 2 represents a histogram expressing the recovery rate of vitamin A propionate respectively at 14 and 28 days of test nos. 12 to 14.

FIG. 2 represents a histogram expressing the recovery rate of vitamin A propionate at 14 and 28 days respectively of tests nos. 12 to 14 and which are indicated in Table 4 above.

Evaluation of the Solubility of Particles of Active Ingredients Obtained According to the Method in Accordance to the Invention:

The solubility of the obtained powders (or in other words, particles of active ingredients) in tests nos. 1 to 14 was tested in hot water at 90° C.

It is seen that the tests prepared according to the invention are insoluble in hot water at 90° C.

Comparative test no. 11 which was prepared by thermal, therefore non-chemical cross-linking, is, as for it, soluble in hot water at 90° C. after one minute of immersion into hot water.

Thus, the particles prepared according to the method in accordance with the invention not only show good stability in a so-called aggressive pre-mix at 14 and 28 days, but also insolubility in hot water at 90° C., and this unlike the chemically cross-linked products.

The invention claimed is:

1. A method for preparing fat-soluble active ingredients, as particles, said method comprises the following steps:
    a) an oil-in-water emulsion is prepared comprising as a percentage by weight based on the total weight of said emulsion including
        8 to 20% of at least one protein,
        5 to 15% of at least one sugar,
        0.5 to 3% of at least one inorganic salt being $NaH_2PO_4$,
        10 to 22% of at least one fat-soluble active ingredient in an oily form and/or dissolved in an edible oil, the active ingredient is selected from the group consisting of Vitamin A, E, D, D3, K, K3, Vitamin A acetate, vitamin A propionate, vitamin A palmitate, tocopheryl acetate, Beta-carotene, lycopene, bixin, zeaxanthin, citranaxanthin, asthaxantin, canthaxanthin, lutein, capsanthin, cryptoxanthin, beta-apo-8'-carotenoic acid, beta-apo-8'-carotenal, beta-apo-12'-carotenal, Omega 3 and omega 6 fatty acids; and
        qsp % of water,
    b) shaping of particles in a substantially spherical shape by the dispersing the oil-in-water emulsion obtained at the end of step a) in a fluid,
    c) adding at least one agent for chemical cross-linking of the at least one protein to the dispersion obtained at the end of step b) the chemical crosslinking does not include heat treatment and is performed at a temperature at the end of step b) which is in a range of about 12° C. to about 45° C., the crosslinking agent is selected from the group consisting of acetaldehyde, glutaraldehyde, and glyoxal, and
    d) the particles of active ingredients with the substantially spherical shape are recovered after step c).

2. The method according to claim 1, wherein said at least one protein is selected from the group consisting of gelatin, casein, caseinate, proteins of soya, and proteins of maize.

3. The method according to claim 1, wherein said at least one sugar is selected from the group consisting of polyols, monosaccharides, disaccharides, glucose syrup, fructose syrup, and maltodextrins.

4. The method according to claim 1, wherein before step a) said at least one active ingredient is dissolved in an edible oil selected from the group consisting of groundnut, sunflower, rapeseed, maize, soya bean, palm and cod liver oil.

5. The method according to claim 1, wherein in step b) of said method, the oil-in-water emulsion is dispersed in an edible oil and step c) further comprises lowering the temperature of the mixture obtained at the end of step b) to a cooling temperature below a phase transition temperature of the protein so as to obtain a dispersion of granules of humid active ingredients in the edible oil to which the agent for crosslinking the protein is added at this cooling temperature.

6. The method according to claim 1, wherein in step b) the oil-in-water emulsion obtained at the end of step a) is dispersed in air by atomization.

7. The method according to claim 5, wherein step d) of said method comprises the following successive steps:
    the granules of active ingredients obtained at the end of step c), are drained, optionally, said granules of active ingredients are absorbed on an anti-agglomerating agent,
    said granules of active ingredients are dried in a fluidized bed so as to recover particles of active ingredients.

8. The method according to claim 1, wherein the size of the particles at the end of step d) is between 50 and 630 μm.

9. The method of claim 1 wherein the at least one protein is 10 to 15%.

10. The method of claim 1 wherein the at least one sugar is 8 to 12%.

11. The method of claim 1 wherein the at least one inorganic salt is 2 to 3%.

12. The method of claim 1 wherein the at least one fat-soluble active ingredient is 15 to 20%.

13. The method of claim 1 wherein the cross linking agent is glutaraldehyde.

14. The method according to claim 1 wherein the particles of active ingredients with the substantially spherical shape which are recovered in step d) have a water content between 1 and 5% by weight.

* * * * *